(12) United States Patent
Patel et al.

(10) Patent No.: US 6,436,132 B1
(45) Date of Patent: Aug. 20, 2002

(54) COMPOSITE INTRALUMINAL PROSTHESES

(75) Inventors: Udayan G. Patel, San Jose, CA (US); Richard S. Stack, Chapel Hill, NC (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/539,258

(22) Filed: Mar. 30, 2000

(51) Int. Cl.$^7$ .................................................. A61F 2/06
(52) U.S. Cl. ...................................... 623/1.13; 623/1.15
(58) Field of Search ............................... 623/1.15, 1.13, 623/1.11, 1.16, 1.18; 606/191, 195, 198

(56) References Cited

U.S. PATENT DOCUMENTS

| | | |
|---|---|---|
| 3,105,492 A | 10/1963 | Jeckel |
| 3,657,744 A | 4/1972 | Ersek |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,531,933 A | 7/1985 | Norton et al. |
| 4,553,545 A | 11/1985 | Maass et al. |
| 4,580,568 A | 4/1986 | Gianturco |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,681,110 A | 7/1987 | Wiktor |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,762,128 A | 8/1988 | Rosenbluth |
| 4,767,418 A | 8/1988 | Deininger et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |

(List continued on next page.)

FOREIGN PATENT DOCUMENTS

| | | |
|---|---|---|
| EP | 0045627 | 2/1982 |
| EP | 0062300 A2 | 10/1982 |
| EP | 0221570 A2 | 5/1987 |

(List continued on next page.)

OTHER PUBLICATIONS

Charnsangavej, Chuslip, M.D., et al., Stenosis of the Vena Cava: Preliminary Assessment of Treatment with Expandable Metallic Stents, *Radiology*, pp. 295–298, vol. 161, Nov. 1986.

(List continued on next page.)

*Primary Examiner*—Kevin Truong
(74) *Attorney, Agent, or Firm*—Fulwider, Patton, Lee & Utecht

(57) ABSTRACT

A composite intraluminal prostheses for treating a stenotic region in a blood vessel. The intraluminal prostheses including a thermally expandable stent and an open cell stent cover where the cell size is selected to be small enough to prevent plaque prolapse and the ingrowth of diseased tissue through the openings in the stent, while allowing for the re-endothelialization of the blood vessel wall with healthy tissue. The stent cover is further able to expand and contract with the stent without becoming loose upon contraction and without exerting significant resistance to radial expansion.

33 Claims, 3 Drawing Sheets

U.S. PATENT DOCUMENTS

| | | |
|---|---|---|
| 4,886,062 A | 12/1989 | Wiktor |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,922,905 A | 5/1990 | Strecker |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,195,984 A | 3/1993 | Schatz |
| 5,197,978 A | 3/1993 | Hess |
| 5,222,971 A | 6/1993 | Willard et al. |
| 5,226,913 A | 7/1993 | Pinchuk |
| 5,234,456 A | 8/1993 | Silvestrini |
| 5,242,452 A | 9/1993 | Inoue |
| 5,282,823 A | 2/1994 | Schwartz et al. |
| 5,282,824 A | 2/1994 | Gianturco |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,356,433 A | 10/1994 | Rowland et al. |
| 5,423,885 A | 6/1995 | Williams |
| 5,617,878 A | 4/1997 | Taheri |
| 5,938,697 A | 8/1999 | Killion et al. |
| 6,071,308 A * | 6/2000 | Ballou et al. .............. 623/1.15 |
| 6,077,296 A * | 6/2000 | Shokoohi et al. .......... 623/1.11 |
| 6,146,417 A * | 11/2000 | Ischinger ................... 623/1.15 |

FOREIGN PATENT DOCUMENTS

| | | |
|---|---|---|
| EP | 0335341 B1 | 10/1989 |
| EP | 0338816 A2 | 10/1989 |
| EP | 0357003 A2 | 3/1990 |
| EP | 0361192 A3 | 4/1990 |
| EP | 0364787 A1 | 4/1990 |
| EP | 0372789 A2 | 6/1990 |
| EP | 0380668 B1 | 8/1990 |
| EP | 0407951 A2 | 1/1991 |
| EP | 0421729 A2 | 4/1991 |
| EP | 0423916 A1 | 4/1991 |
| EP | 0428479 B1 | 5/1991 |
| EP | 0517075 B1 | 12/1992 |
| EP | 0540290 B1 | 5/1993 |
| EP | 0541443 A1 | 5/1993 |
| EP | 0 795 304 A1 | 9/1997 |
| EP | 0 938 879 A2 | 9/1999 |
| EP | 0 960 607 A1 | 12/1999 |
| FR | 2677872 | 12/1992 |
| GB | 2070490 A | 9/1981 |
| GB | 2135585 A | 9/1984 |
| JP | 58-501458 | 9/1983 |
| JP | 62 231657 | 10/1987 |
| JP | 62235496 A * | 10/1987 |
| JP | 63-214264 * | 9/1988 |
| JP | 01083685 A * | 3/1989 |
| JP | 1-299550 * | 12/1989 |
| JP | 02-174859 * | 7/1990 |
| JP | 02-255157 * | 10/1990 |
| JP | 3-9745 * | 1/1991 |
| JP | 03009746 A * | 1/1991 |
| JP | 3-151983 * | 6/1991 |
| JP | 04-25755 * | 2/1992 |
| WO | WO91/07139 | 5/1991 |
| WO | WO92/06734 | 4/1992 |
| WO | WO92/09246 | 6/1992 |
| WO | WO97/25937 * | 7/1997 |
| WO | WO98/20927 * | 5/1998 |
| WO | WO 98/20928 | 5/1998 |
| WO | WO98/32412 * | 7/1998 |
| WO | WO 98/38946 | 9/1998 |
| WO | WO 98/40035 | 9/1998 |
| WO | WO99/17680 * | 4/1999 |
| WO | WO99/39661 * | 8/1999 |

OTHER PUBLICATIONS

Rösch, Josef, M.D., et al., Experimental Intrahepatic Portacaval Anastomosis: Use of Expandable Gianturco Stents, *Radiology*, pp. 481–485, vol. 162, No. 1987.

Rösch, Josef, M.D., et al., Modified Gianturco Expandable Wire Stents in Experimental and Clinical Use, *Annales de Radiologie*, pp. 100–103, vol. 31, No. 2, 1998.

Lawrence, David D., Jr., et al., Percutaneous Endovascular Graft: Experimental Evaluation, *Radiology*, pp. 357–360, vol. 163, May 1987.

Rösch, Josef, et al., Gianturco Expandable Stents in Experimental and Clinical Use, pp. 121–124. Twelfth Annual Course on "Diagnostic Angiography and Interventional Radiology" Mar. 23–26, 1987, San Diego, California.

Dotter, Charles T., Transluminally Placed Coilspring Endarterial Tube Grafts, *Investigative Radiology*, pp. 329–332, Sep./Oct. 1969.

Rösh, J., M.D., et al., Transjugular intrahepatic Portacaval Shunt: An Experimental Work, *The American Journal of Surgery*, pp. 588–592, vol. 121, May 1971.

Dotter, Charles T., Transluminal Expandable Nitinol Coil Stent Grafting: Preliminary Report, *Radiology Journal*, pp. 259–260, Apr. 1983.

Cragg, et al., Non–Surgical Placement of Arterial Endoprostheses: A New Technique Using Nitinol Wire, *Radiology Journal*, pp. 261–263, Apr. 1983.

Maas, et al., Radiological Follow–Up Transluminally Inserted Vascular Endoprostheses; An Experimental Study Using Expanding Spirals, *Radiology Journal*, pp. 659–663, 1984.

70th Scientific Assembly and Annual Meeting: Scientific Program, *Radiology*, Washington, DC: Nov. 25–30, 1084, Special Edition, vol. 153(P).

C. R. Bard, PE Plus Peripheral Balloon Dilatation Catheter, *C. R. Bard, Inc.*, Aug. 1985.

Wright, et al., Percutaneous Endovascular Stents: An Experimental Evaluation, *Radiology Journal*, pp. 69–72, 1985.

Palmaz, et al., Expandable Intraluminal Graft; A Preliminary Study, *Radiology Journal*, pp. 73–77, 1985.

Program: Day 2 (Nov. 18) The Radiological Society of North America, *Radiology*, 1985.

Charnsangavej, C., M.D., et al., Endovascular Stent for Use in Aortic Dissection: An In Vitro Experiment, *Radiology*, pp. 323–324, vol. 157, No. 2, Nov. 1985.

Wallace, Michael J., et al., Tracheobronchial Tree: Expandable Metallic Stents Used in Experimental and Clinical Applications (Work In Progress), *Radiology*, pp. 309–312, vol. 158, Feb. 1986.

72nd Scientific Assembly and Annual Meeting: RSNA Scientific Program, *Radiology*, Chicago: Nov. 30–Dec. 5, 1986, Special Edition vol. 161(P).

Duprat, et al., Flexible Balloon–Expanded Stent for Small Vessels, *Radiology Journal*, pp. 276–278, 1987.

Rösch, Josef, M.D., et al., Gianturco Expandable Stents in Experimental and Clinical Use, paper presented at The Twelfth Annual Course on "Diagnostic Angiography and Interventional Radiology" Mar. 23–26, 1987 (San Diego, California).

Rösch, Joseph, M.D., et al., Gianturco Expandable Wire Stents in the Treatment of Superior Vena Cava Syndrome Recurring After Maximum–Tolerance Radiation, *Cancer*, pp. 1243–1246, vol. 60, Sep. 1987.

Yoshioka, Tetsuya, et a., Self–Expanding Endovascular Graft: An Experimental Study in Dogs, *American Journal of Roentgeriology*, pp. 673–676, vol. 151, Oct. 1988.

Yoshioka, et al., Developemnt and Clinical Application of Biliary Endoprostheses Using Expandable Metallic Stents, *Japan Radiological Society*, 1988, vol. 48, No. 9, pp. 1183–1185 (with translation).

Mirich, et al., "Percutaneously Placed Endovascular Grafts for Aortic Aneurysms: Feasibility Study", *Radiology*, 1989, Part 2, pp. 1033–1037.

\* cited by examiner

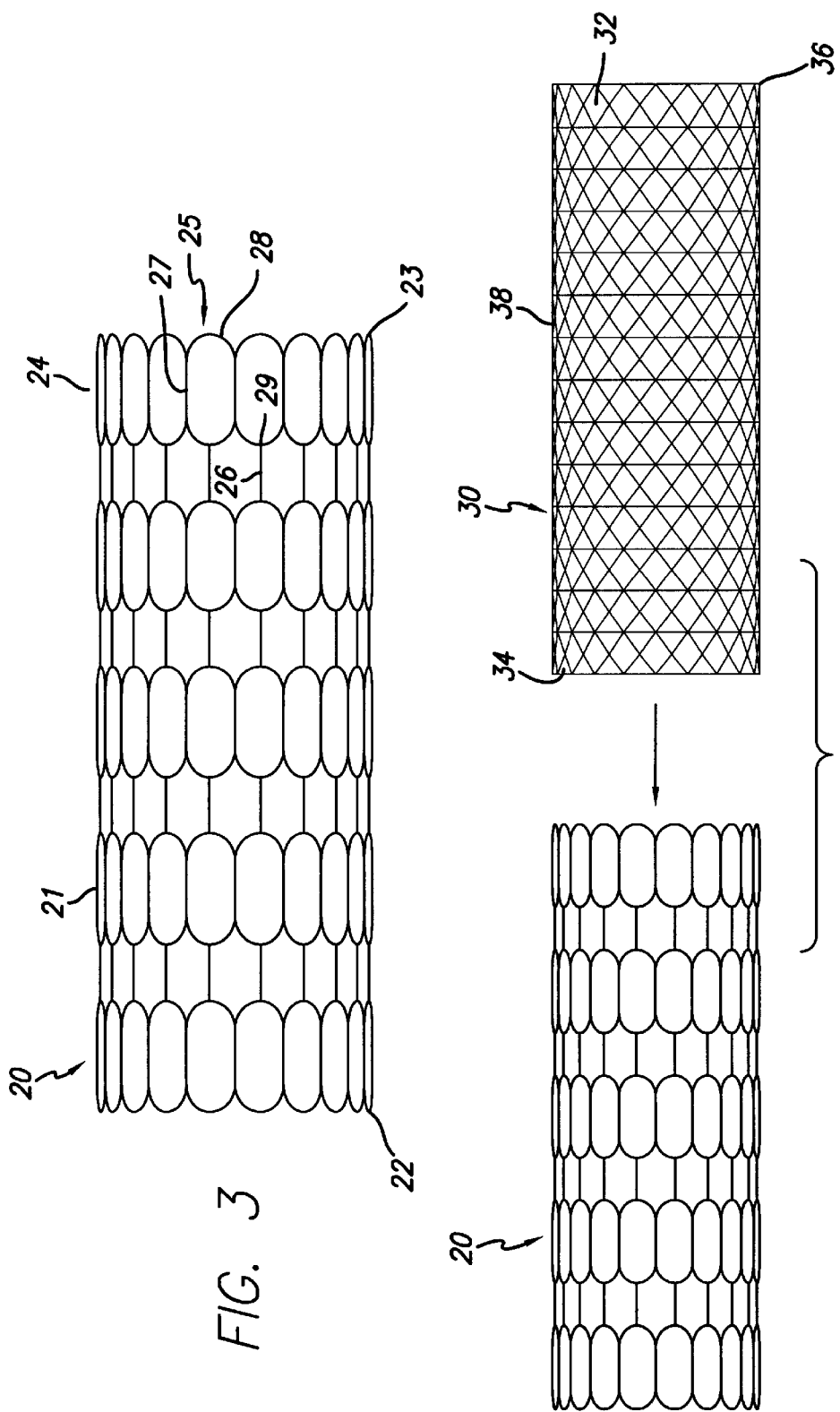

COMPOSITE INTRALUMINAL PROSTHESES

BACKGROUND OF THE INVENTION

The present invention is directed generally to the field of expandable intraluminal prostheses, commonly referred to as stents, and more particularly to a composite device including a thermally expandable stent and an open mesh stent cover.

Stents are typically used as adjuncts to percutaneous transluminal balloon angioplasty procedures, in the treatment of occluded or partially occluded arteries and other blood vessels. In a typical balloon angioplasty procedure, a guiding catheter or sheath is percutaneously introduced into the cardiovascular system of a patient through the femoral arteries and advanced through the vasculature until the distal end of the guiding catheter is positioned at a point proximal to the lesion site. A guidewire and a dilatation catheter having a balloon on the distal end are introduced through the guiding catheter with the guidewire sliding within the dilatation catheter. The guidewire is first advanced out of the guiding catheter into the patient's vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressure to radially compress the atherosclerotic plaque of the lesion against the inside of the artery wall and thereby dilate the lumen of the artery. The balloon is then deflated to a small profile so that the dilatation catheter can be withdrawn from the patient's vasculature and blood flow resumed through the dilated artery. As should be appreciated by those skilled in the art, while the above-described procedure is typical, it is not the only method used in angioplasty.

Balloon angioplasty sometimes results in short or long term failure. That is, vessels may abruptly close shortly after the procedure or gradual restenosis may occur for months thereafter. To counter the tendency of recurrent vessel occlusion following angioplasty, implantable intravascular prostheses, commonly referred to as stents, have emerged as a means by which to achieve long term vessel patency. Stated simply, a stent functions as permanent scaffolding to structurally support the vessel wall and thereby maintain luminal patency. Stents are typically small expandable metallic tubes having interconnecting spans and struts which form a generally open cellular construction. Stents are transported to a lesion site by means of a delivery catheter.

There are several types of stents mainly, balloon expandable stents, spring-like self-expandable stents, or thermally expandable stents. Balloon expandable stents are delivered by means of a dilitation catheter and are plastically deformed by means of an expandable member, such as an inflation balloon, from a small initial diameter to a larger expanded diameter. Self-expanding stents are formed as spring elements which are radially compressible about a delivery catheter. A compressed self-expanding stent is typically held in the compressed state by a delivery sheath. Upon delivery to a lesion site, the delivery sheath is retracted allowing the stent to expand. Thermally expandable stents are formed from shape memory alloys which posses the ability to expand from a small initial diameter to a second larger diameter upon the application of heat to the alloy. Although each method of stent expansion is effective, self-expanding stents tend to be difficult to deploy accurately, and balloon expandable stents may, in rare circumstances, inflict undesirable trauma on particularly fragile vessels.

Details of prior art expandable stents can be found in U.S. Pat. No. 3,868,956 (Alfidi et al.); U.S. Pat. No. 4,512,1338 (Balko et al.); U.S. Pat. No. 4,553,545 (Maass, et al.); U.S. Pat. No. 4,733,665 (Palmaz); U.S. Pat. No. 4,762,128 (Rosenbluth); U.S. Pat. No. 4,800,882 (Gianturco); U.S. Pat. No. 5,514,154 (Lau, et al.); U.S. Pat. No. 5,421,955 (Lau et al.); U.S. Pat. No. 5,603,721 (Lau et al.); U.S. Pat. No. 4,655,772 (Wallsten); U.S. Pat. No. 4,739,762 (Palmaz); and U.S. Pat. No. 5,569,295 (Lam), which are hereby incorporated by reference.

While stents alone perform adequately for the purpose of holding open otherwise occluded, partially occluded, or weakened blood vessels, due to the open structure of a stent there is a tendency for a stent to permit the passage of material through the stent body. Such material may include excessive cell or tissue growth, thrombus formations, and plaque. These materials may have a tendency to block or otherwise re-occlude the open vessel.

One technique to reduce the susceptibility for materials to pass through the wall of a deployed stent includes providing the stent with an outer covering formed from a biocompatible polymer surrounding the open stent construction. One such material commonly used for this purpose is GORE-TEX Vascular Graft (W. L. Gore & Associates, Inc, Flagstaff, Ariz.), which is a micro porous polymer film. The stent cover, however, presents somewhat of a problem in that some transfer of cellular material through the cover is generally desirable. If the cover material is porous, then cells, tissue, and capillaries can penetrate the pores, allowing the blood vessel to be re-endothelialized with new healthy tissue. However, if the covering is too porous, there may be a tendency for diseased tissue to transfer itself to the newly created intima and damage healthy tissue. Micro porous materials like GORE-TEX Vascular Graft have pore sizes on the order of 10–100 microns and are effective at preventing diseased tissue ingrowth. However, due to the very small pore size, re-endothelialization with new healthy tissue may be somewhat compromised. Also, the stent cover material must be sufficiently flexible and expandable to permit deployment of the stent from its initial diameter to its deployed diameter. Many non-porous and micro-porous films, when formed as tubular covers, do not readily expand in the radial direction. For this reason most prior art stent covers are either foldable or have an overlapping slidable design to permit stent expansion. Typically, the covers are attached to the stent along a single seam running along the length of the stent. Thus, the covers may slip or deploy non-uniformly during stent expansion.

What is needed, therefore, is a composite intraluminal prosthesis including a stent and a macro-scale outer mesh covering which fits over the stent and presents little or no resistance to radial expansion. In addition, the cell size of the mesh cover should be large enough to allow re-endothelialization of the diseased blood vessel wall with healthy tissue and should be small enough to prevent plaque prolapse or the growth of diseased tissue within the open structure of the stent. Further, it maybe desirable for the underlying stent to be of the thermally expandable type in order to minimize vessel trauma which may be caused by balloon expandable stents or other self-expanding stents. The present invention satisfies these and other needs.

SUMMARY OF THE INVENTION

The present invention is an intraluminal prosthesis or covered stent comprising a tubular expandable stent having an open cell mesh stent cover. The stent has an exterior surface, a luminal surface, and plurality of openings through the wall to provide scaffolding support for the stent cover. The stent can be formed from a two-way shape memory alloy. Particular use is made of the thermal expansion properties of the shape memory alloy to provide a stent which expands and implants itself within a blood vessel without inflicting trauma to the vessel lumen. The stent cover can be formed from a mesh having an open, square or diamond cell pattern. The particular cell size of the mesh is selected so as to prevent plaque prolapse and the ingrowth of diseased tissue through the openings in the stent, thereby inhibiting possible re-occlusion of the vessel. The mesh cell size is further selected to allow for the re-endothelialization of the vessel wall with healthy tissue. The stent cover is able to expand and contract with the underlying stent without becoming loose if contracted and without exerting significant resistance to radial expansion.

Other features and advantages of the present invention will become apparent from the following detailed description.

BRIEF DESCRIPTION OF THE DRAWINGS

FIG. 3 is a side view of a stent embodying features of the invention as shown in an expanded or deployed position.

FIG. 4 is a side view of a stent cover embodying features of the invention shown in an expanded position, and of the stent of FIG. 3, showing the relationship between the stent and the stent cover.

DETAILED DESCRIPTION OF THE PREFERRED EMBODIMENTS

Figure 1:
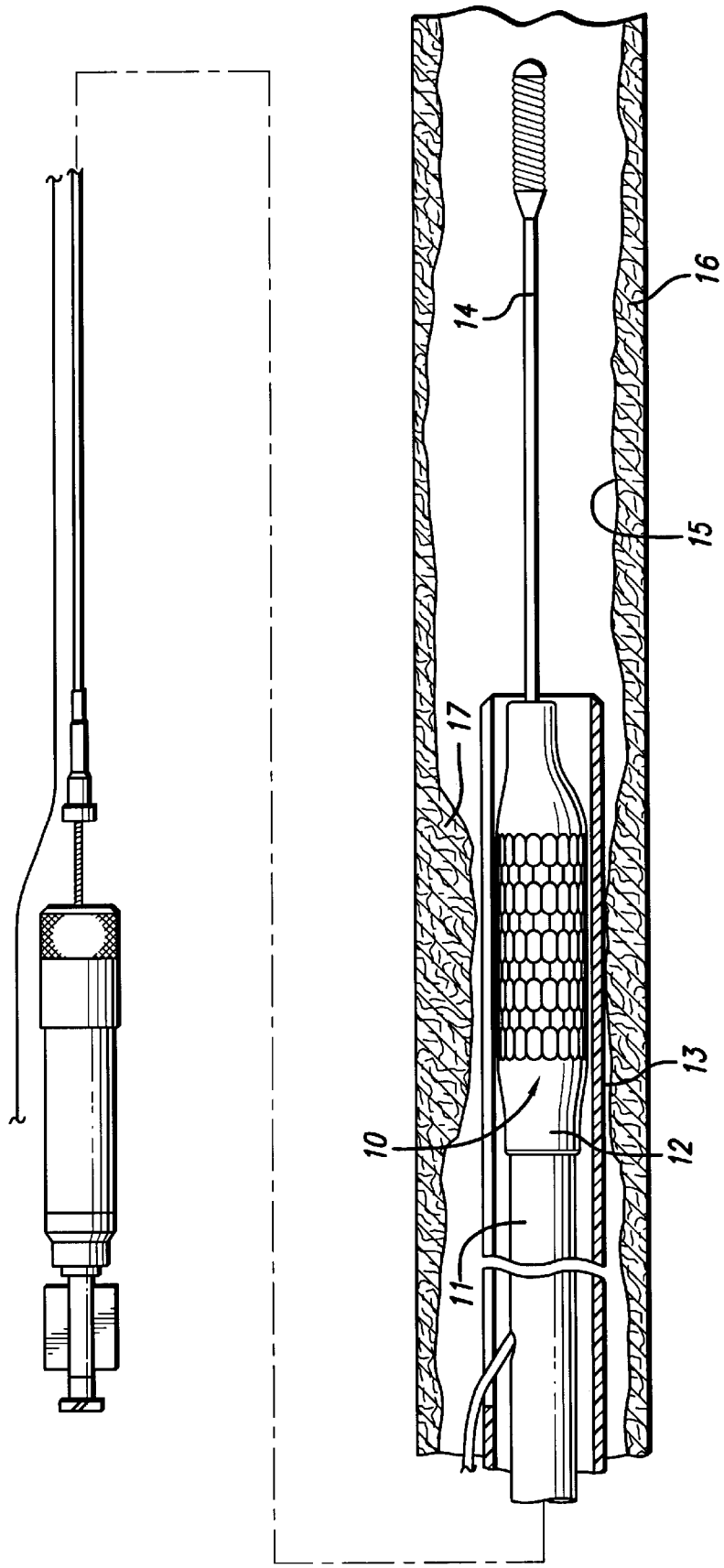
FIG. 1 is an elevational view, partially in section, of an intraluminal prosthesis embodying features of the invention which is mounted on a delivery catheter and disposed within a diseased artery.

FIG. 1, illustrates a composite intraluminal prosthesis 10 in accordance with the present invention which is mounted on a delivery catheter 11. The delivery catheter 11 includes a balloon 12 or other member capable of holding a volume of liquid. Referring now to FIGS. 3 and 4, the composite intraluminal prosthesis 10 includes a thermally expandable stent 20 formed from a shape memory alloy and having an open mesh stent cover 30 which presents little resistance to radial expansion.

The stent 10 of the present invention can be made of a wide variety of two-way shape memory alloys. A particularly suitable material is Nitinol a nickel titanium binary alloy. Other alloys such as Ni—Ti—X (X being V, Co, Cu, Fe) ternary alloys, Cu—Al—Ni ternary alloys and Cu—Zn—Al ternary alloys are also suitable. A two-way shape memory material is characterized by having a low temperature martensitic phase and a high temperature austenitic phase and by the ability to transit between the two phases whenever the material's temperature passes below the martensitic phase transition temperature ("T1") or above the austenitic phase transition temperature ("T2"). These two transition temperatures are intrinsic characteristics of the material. Typically shape memory alloys are soft and flexible in their martensitic phase and are hard and ridged in their austenitic phase.

In particular, if shape memory alloys are cooled below the transition temperature T1 such that they are in the martensitic phase, and are then stressed sufficiently to physically deform them into what is an apparently permanent new shape, upon heating above the transition temperature T2, all of the deformation which occurred in the martensitic phase will be reversed and the original shape will be recovered. That is the deformed object will simply revert to the shape in which it existed prior to the cycle of cooling, deformation and reheating.

In accordance with the present invention particularly good use can be made of the characteristics of shape memory alloys by fabricating the stent in a desired expanded shape while the material is in the high temperature austenitic phase and subsequently cooling the stent to the low temperature martensitic phase and deforming the stent to a low profile about a delivery catheter. Upon delivery to a lesion site, the stent may be reheated and will thereby expand to its original diameter.

In accordance with the present invention, the shape memory alloy should have an austenitic transition temperature T2 above the mean human body temperature of about 37 degrees Celsius. Austenitic transition temperatures in the range of about 40 to 80 degrees Celsius are suitable. In addition, the material should have a martensitic transition temperature T1 below mean human body temperature. Suitable martensitic transition temperatures are in the range of about −10 to 30 degrees Celsius.

Referring now to FIG. 3, the stent 20 comprises a tubular body 21 having a longitudinal axis, a proximal edge 22, and a distal edge 23. The tubular body 21 is formed from a plurality of spaced apart rings 24 which are composed of a plurality of adjacent deformable oval scaffolding elements 25, which may be compressed radially inwardly about the catheter balloon 12, when the stent 20 is chilled below its martensitic transition temperature T1. The rings 24 of the scaffolding elements 25 are interconnected by a plurality of connecting links 26. When viewed in isolation, each continuous oval element 25 includes a pair of opposing straight parallel longitudinal struts 27 and a pair of opposing semicircular sectors 28. Each of the semicircular sectors 28 has a midpoint 29. The struts 27 are connected at each end to the semicircular sectors 28 to form the continuous oval element 25.

As formed on the stent 20, each longitudinal strut 27 is shared by each adjacent oval element 25. Thus, each oval element 25 is connected to each adjacent oval element 25 by the struts 27. To form the rings 24, the oval elements 25 are evenly spaced angularly at a constant radius about the longitudinal axis of the stent. Each oval element 25 in each ring 24, is coaxially aligned with the other oval elements 25 in the spaced apart rings 24, so as to form rows of oval elements 25 along the length of the tubular body 21. Each oval element 25 is connected to the next coaxially aligned oval element 25 in the adjacent rings 24 by the longitudinal connecting elements 26. Each individual connecting element 26 is connected at each end to the midpoints 29 of each opposing semicircular sector 28 of the coaxially aligned oval elements 25.

Generally, each oval element 25 possesses an aspect ratio of about 2:1. That is, the length of the struts 27 are about twice as long the diameter of the semicircular sectors 28. An aspect ratio of 2:1 provides for good shape recovery upon reheating to the material's austenitic phase after cooling to the martensitic phase and subsequent deformation to a low profile delivery diameter. In addition, an aspect ratio of 2:1 provides good scaffolding support for the mesh cover 30 and provides sufficient resistance against blood vessel recoil to prevent radial collapse of the stent 20. The thickness of the struts 27 and the semicircular elements 28 vary dependant on the degree of radial strength required for the particular application.

The length of the interconnecting links 26 varies dependant on the degree of scaffolding support required. Generally, a link length approximately equal to the diameter of the semicircular elements 28 provides good support.

In one particulaly preferred embodiment of the stent 20, the overall length of the oval elements 25 is about 2 mm and the corresponding width of the elements is about 1 mm. The length of the interconnecting links 26 is also about 1 mm.

Figure 5:
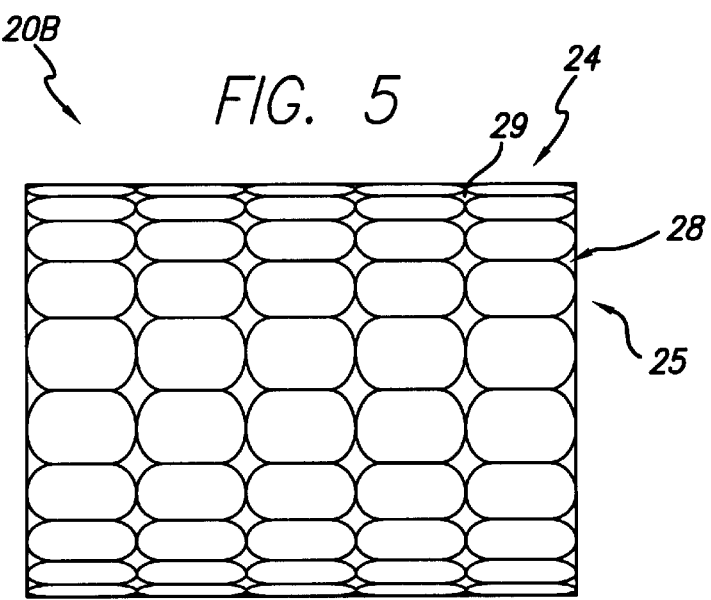
FIG. 5 is an another embodiment of a stent embodying features of the present invention.

An alternative embodiment of the stent 20b is shown in FIG. 5. In this embodiment the interconnecting links 26 are removed and each ring 24 of oval elements 25 is connected to each adjacent ring 24 at the midpoints 29 of each opposing semicircular sector 28.

The above-described embodiments of the stent 20 are meant to be exemplary and should not be construed as limiting. The elements 25 may be ellipsoidal rather than oval, with the major and minor axes of the ellipse possessing an aspect ratio of about 2:1. Further, in an embodiment where the interconnecting links 26 are used, the links need not be connected between each adjacent element. In some circumstances, particularly where a high degree of stent flexibility is required it may be preferable to have as few as one interconnecting link 26 between each ring of elements 24.

The stent 20 of the present invention can be made by a number of methods known to those skilled in the art. One method is to laser cut or electro-discharge machine the stent pattern from drawn tubing made of shape memory material. Stents made by these methods are typically finished by electro-polishing which is also known to those skilled in the art. Other methods of making stents are also suitable such as chemical etching.

Referring now to FIG. 4, the mesh cover 30 comprises an elongated open mesh tube 38 with a proximal edge 34, a distal edge 36, and a repeating pattern of square shaped cells 32. Other cell shapes such as a repeating diamond pattern are also suitable. The cells 32 should be small enough to prevent plaque prolapse and the ingrowth of diseased tissue, yet should be large enough to allow for re-endothelialization of the vessel wall with healthy tissue. A cell size within a range of about 0.2 mm to 1.5 mm square is suitable, with 1 mm square being preferred.

The mesh cover 30 must be able to expand and contract along with the stent 10 to which the cover is attached. The mesh cover 30 should not exert significant resistance to radial expansion and should not become loose or "bunch up" when the stent is compressed to its low profile delivery diameter. One preferred material which has these properties is expanded polytetrafluorothylene (PTFE). Other materials such as polyurethane are also suitable. Typically, expanded PTFE is made by pulling or expanding the PTFE in the longitudinal direction after extrusion. Expanded PTFE is capable of being pushed or pulled between a shorter and longer length without stretching or exerting significant resistance against expansion when going from the shorter to the longer length. To best take advantage of the properties of expanded PTFE, it is preferred, though not required, that the PTFE be spirally wrapped, as shown in FIG. 3, so that each filament of the mesh is angularly offset from the longitudinal axis of the stent 20.

The expanded PTFE mesh may be made by weaving, braiding, or knitting PTFE filaments about a mandrel. These methods and others are known to those skilled in the art. The mesh cover 30 is affixed to the stent 20 with an adhesive. The adhesive may be a thermoplastic adhesive and preferably a thermoplastic fluoropolymer adhesive such as fluorinated ethylene propylene ("FEP"). The mesh cover 30 may be affixed to each individual cell 25 and strut 26 of the stent 20. Alternatively, the cover 30 may be fixed along its proximal and distal edges 34 and 36 to the corresponding proximal and distal edges 22 and 23 of the stent 20.

Figure 2:
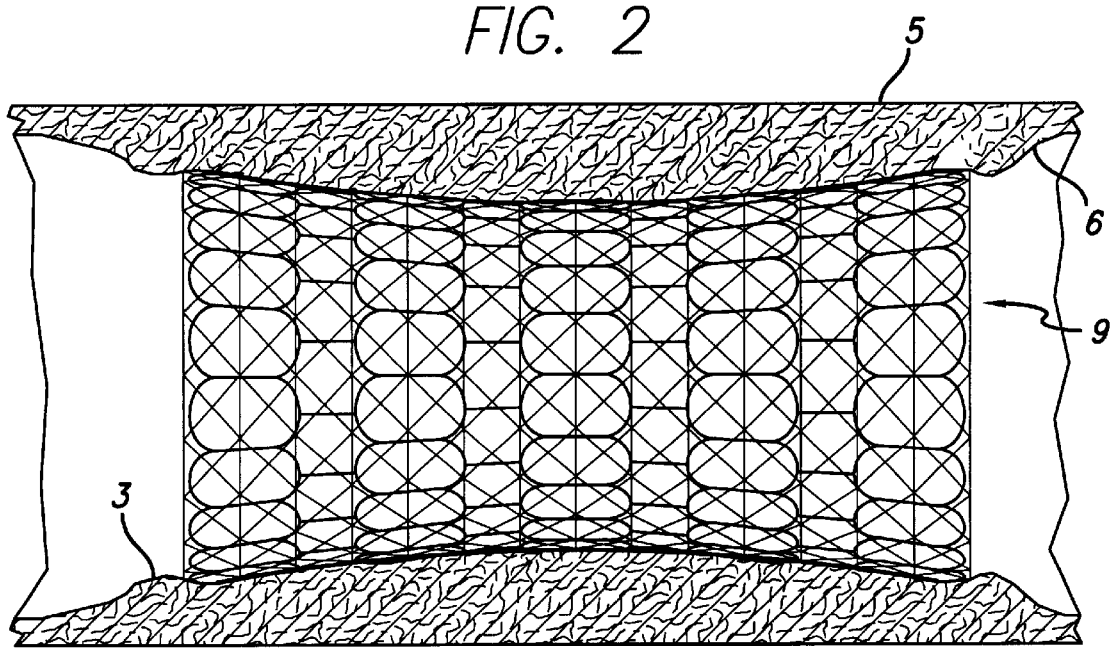
FIG. 2 is an elevational view, partially in section, showing the expanded intraluminal prosthesis within the artery after withdrawal of the delivery catheter.

Referring now to FIGS. 1–2, the covered stent 10 of the present invention is used as follows. A balloon angioplasty procedure is performed at the site of a lesion 17 within an interior lumen 15 of a blood vessel 16. Subsequently, the covered stent 10 is chilled below its martensitic transformation temperature (T1), causing the shape memory alloy to transition to its soft martensitic state. Upon being chilled to below T1, the covered stent 10 is compressed from its first diameter corresponding to its austenitic phase to a second smaller or low profile delivery diameter. The stent may then be crimped into place. Typically, the covered stent 10 will be compressed to its low profile diameter after being slipped over the catheter balloon 12. The covered stent 10 will retain its second small or low profile diameter as long as it is in its martensitic phase. Preferably, the catheter 11 and the balloon 12 are initially filled with chilled saline solution to keep the covered stent 10 in its martensitic state during delivery.

Generally, prior to preparing the covered stent 10 for delivery, a guiding catheter 4 has been placed in the patient's vasculature and advanced through the body lumen 5 to a point proximal of the lesion 17. A guidewire 14 has also been advanced through the guiding catheter 13 and is advanced out of the guiding catheter across the lesion 17 to a point distal of the lesion. Often, the guiding catheter and guidewire that were used during the angioplasty procedure are left in place in the patient and reused during the stent placement procedure. The delivery catheter 11 and covered stent 10 are subsequently advanced over the guidewire 14 until the covered stent 10 is positioned across the lesion 17. Once positioned across the lesion 17, the catheter 11 is flushed with warm saline solution to heat the covered stent 10 above its austenitic transformation temperature (T2). Upon reaching T2, the covered stent 10 expands to its as machined (first) diameter, or austenitic state diameter and conforms with and supports the blood vessel wall. The mesh 30 expands with the stent and engages the inner surface of the vessel lumen 15, thereby preventing plaque prolapse and the ingrowth of diseased tissue. After expansion, the delivery catheter 11 is withdrawn leaving the expanded covered stent 10 in place within the blood vessel 16 as shown in FIG. 2.

It should be noted that the catheter 11 is not used to expand the covered stent 10 as with balloon expandable stents. Here, the balloon catheter 11 serves to deliver the covered stent 10, to cool the stent prior to delivery, and to heat the stent upon delivery to the lesion 17. As will be appreciated by those skilled in the art, catheter-like devices built specifically for delivering a thermally expandable stent may be used in place of the balloon catheter 1.

It will be appreciated that a new form of covered stent has been presented. While only the presently preferred embodiment has been described in detail, as will be apparent to those skilled in the art, modifications and improvements may be made to the device disclosed herein without departing from the scope of the invention. Accordingly, it is not intended that the invention be limited except as by the appended claims

What is claimed is:

1. A thermally expandable intraluminal prostheses for implanting in a body lumen comprising an expandable stent body, the stent body having a first configuration having a first diameter at temperature T2 and having a second configuration having a second diameter at temperature T1, wherein the second diameter is smaller than the first diameter and temperature T1 is lower than temperature T2; and an expandable polymer open cell mesh cover coupled with the expandable stent body, wherein the polymer mesh cover exhibits minimal resistance to radial expansion and has a multiplicity of cell openings greater than 100 microns in width.

2. The intraluminal prostheses of claim 1, wherein the stent body includes a plurality of spaced apart coaxially aligned rings, each ring comprising a plurality of oval elements having straight sides and semicircular ends;

the oval elements being connected adjacent to each other along the straight sides, wherein each oval element is angularly displaced from the next at a constant radius; and a plurality of connecting elements for interconnecting the spaced apart rings, wherein the connecting elements connect the semicircular ends of the oval elements which form the rings.

3. The intraluminal prostheses of claim 2, wherein the oval elements have an aspect ratio of 2:1.

4. The intraluminal prostheses of claim 2, wherein the oval elements have an overall length of 2 mm and the semicircular ends of a radius of 0.5 mm.

5. The intraluminal prostheses of claim 2, wherein the connecting links have a length of 1 mm.

6. The intraluminal prostheses of claim 2, wherein the expandable polymer mesh cover has square shaped cells.

7. The intraluminal prostheses of claim 6, wherein the square shaped cells are 1 mm square.

8. The intraluminal prostheses of claim 2, wherein the expandable polymer mesh cover has diamond shaped cells.

9. The intraluminal prostheses of claim 2, wherein the expandable polymer mesh cover is made from expanded polytetrafluorothylene.

10. The intraluminal prostheses of claim 2, wherein the expandable polymer mesh cover is made is bonded to each cell of the stent body.

11. The intraluminal prostheses of claim 2, wherein the proximal and distal edges of the expandable polymer mesh cover are bonded to the proximal and distal edges of the stent body.

12. The intraluminal prostheses of claim 1, wherein the stent body includes a plurality of adjacent coaxially aligned rings, each ring comprising a plurality of oval elements having straight sides and semicircular ends;

the oval elements being connected adjacent to each other along the straight sides, wherein each oval element is angularly displaced from the next at a constant radius; and each ring of oval elements being connected to the oval elements in adjacent rings at the semicircular ends.

13. The intraluminal prostheses of claim 12, wherein the oval elements have an aspect ratio of 2:1.

14. The intraluminal prostheses of claim 12, wherein the oval elements have an overall length of 2 mm and the semicircular ends of a radius of 0.5 mm.

15. The intraluminal prostheses of claim 12, wherein the expandable polymer mesh cover has square shaped cells.

16. The intraluminal prostheses of claim 15, wherein the square shaped cells are 1 mm square.

17. The intraluminal prostheses of claim 12, wherein the expandable polymer mesh cover has diamond shaped cells.

18. The intraluminal prostheses of claim 12, wherein the expandable polymer mesh cover is made from expanded polytetrafluorothylene.

19. The intraluminal prostheses of claim 12, wherein the expandable polymer mesh cover is made is bonded to each cell of the stent body.

20. The intraluminal prostheses of claim 12, wherein the proximal and distal edges of the expandable polymer mesh cover are bonded to the proximal and distal edges of the stent body.

21. The intraluminal prostheses of claim 1, wherein the stent body is made from a shape memory material.

22. The intraluminal prostheses of claim 1, wherein the stent body is made from a material selected from the group consisting of NiTi binary alloys, Ni—Ti—X (X being V, Co, Cu, Fe) ternary alloys, Cu—Al—Ni ternary alloys, and Cu—Zn—Al ternary alloys.

23. The intraluminal prostheses of claim 1, wherein the stent body is made from nitinol.

24. The intraluminal prostheses of claim 1, wherein the expandable polymer mesh cover has square shaped cells.

25. The intraluminal prostheses of claim 24, wherein the square shaped cells are 1 mm square.

26. The intraluminal prostheses of claim 1, wherein the expandable polymer mesh cover has diamond shaped cells.

27. The intraluminal prostheses of claim 1, wherein the expandable polymer mesh cover is made from expanded polytetrafluorothylene.

28. The intraluminal prostheses of claim 1, wherein the expandable polymer mesh cover is made is bonded to each cell of the stent body.

29. The intraluminal prostheses of claim 1, wherein the proximal and distal edges of the expandable polymer mesh cover are bonded to the proximal and distal edges of the stent body.

30. The intraluminal prostheses of claim 1, wherein the expanded polymer open cell mesh cover is made from braided filaments of expanded polytetrafluoroethylene.

31. The intraluminal prostheses of claim 30, wherein the expandable polymer open cell mesh cover is applied to the stent body by thermoplastic adhesive.

32. The intraluminal prostheses of claim 1, wherein the multiplicity of cell openings are greater than about 0.2 mm in width.

33. The intraluminal prostheses of claim 1, wherein the multiplicity of cell openings are between about 0.2 mm to about 1.5 mm in width.

* * * * *

UNITED STATES PATENT AND TRADEMARK OFFICE
CERTIFICATE OF CORRECTION

PATENT NO. : 6,436,132 B1
DATED : August 20, 2002
INVENTOR(S) : Udayan G. Patel

It is certified that error appears in the above-identified patent and that said Letters Patent is hereby corrected as shown below:

Column 7,
Lines 46, 47 and 48, change "the proximal", to read -- proximal --, (two places).
Lines 2 through 8, should be reformatted to appear as follows:
-- 1. A thermally expandable intraluminal protheses
for implanting in a body lumen comprising:
an expandable stent body, the stent body having
a first configuration having a first diameter at
temperature T2 and having a second configuration
having a second diameter at temperature T1,
wherein the second diameter is smaller than the
first diameter and temperature T1 is lower than
temperature T2; and --.

Column 8,
Lines 17, 18 and 19, change "the proximal", to read -- proximal --, (two places).
Lines 42, 43 and 44, change "the proximal", to read -- proximal --, (two places).

Signed and Sealed this

Twenty-eighth Day of January, 2003

JAMES E. ROGAN
*Director of the United States Patent and Trademark Office*